(12) United States Patent
Weizenegger

(10) Patent No.: US 7,579,454 B2
(45) Date of Patent: Aug. 25, 2009

(54) METHOD FOR DETECTING GRAM-POSITIVE BACTERIA

(75) Inventor: Michael Weizenegger, Wiesloch (DE)

(73) Assignee: Hain Lifescience GmbH, Nehren (DE)

( * ) Notice: Subject to any disclaimer, the term of this patent is extended or adjusted under 35 U.S.C. 154(b) by 349 days.

(21) Appl. No.: 10/476,506

(22) PCT Filed: Apr. 9, 2002

(86) PCT No.: PCT/EP02/03956

§ 371 (c)(1),
(2), (4) Date: Oct. 31, 2003

(87) PCT Pub. No.: WO02/097126

PCT Pub. Date: Dec. 5, 2002

(65) Prior Publication Data

US 2004/0171007 A1    Sep. 2, 2004

(30) Foreign Application Priority Data

May 3, 2001   (DE)   ................................. 101 21 505

(51) Int. Cl.
*C07H 21/04* (2006.01)
*C07H 21/02* (2006.01)
*C07H 21/00* (2006.01)
*C12Q 1/00* (2006.01)
*C12Q 1/68* (2006.01)

(52) U.S. Cl. .................. 536/24.32; 536/23.1; 536/23.7; 536/24.3; 536/25.32; 435/4; 435/6; 435/40.5; 435/91.2; 435/287.2

(58) Field of Classification Search ...................... 435/4, 435/6, 40.5, 91.2, 287.2; 536/23.1, 23.7, 536/24.3, 25.32, 24.32
See application file for complete search history.

(56) References Cited

U.S. PATENT DOCUMENTS 5,703,217 A    12/1997   Mabilat et al.
6,294,328 B1 *  9/2001   Fleischmann et al. .......... 435/6
6,583,266 B1 *  6/2003   Smith et al. ................. 530/350

FOREIGN PATENT DOCUMENTS

DE    1 390 541    10/2005

OTHER PUBLICATIONS

English translation of International Preliminary Examination Report.
Roller C., et al., "Gram-positive bacteria with a high DNA G+C content are characterized by a common insertion within their 23S rRNA genes," Journal of General Microbiol 1992; 138: 1167-1175.
Roller C., et al., "In situ probing of Gram-positive bacteria with high DNA G+C content using 23S rRNA-targeted oligonucleotides," Microbiol 1994; 140: 2849-2858.
Database EMBL 'Online!' EBI; May 24, 1996, Cole S.T. et al.: "Mycobacterium tuberculosis H37Rv complete genome; segment 59/162" retrieved from http://www.EBI.AC.UK, Database accession No. Z73902; XP002228144.
Hügle B., et al., "A Closer Look at the Insertion within Helix 54 of the 23S-rRNA of the Genus *Corynebacterium* (and Related Taxa)," Clin. Lab. 2000; 46: 255-260.
Fu L., et al., "Is *Mycobacterium tuberculosis* a closer relative to Gram-positive or Gram-negative bacterial pathogens?" Tuberculosis 2002; 82(2/3): 85-90.
International Search Report for PCT Application No. PCT/EP02/03956, issued by the European Patent Office on Mar. 6, 2003.

* cited by examiner

*Primary Examiner*—Rodney P. Swartz
(74) *Attorney, Agent, or Firm*—Dobe Law Group, LLC; Christopher Aniedobe

(57) ABSTRACT

The present invention relates to a method for detecting and/or identifying Gram-positive bacteria with high GC content, in particular mycobacteria. The method comprises a nucleic acid amplification reaction and a subsequent hybridization reaction with suitable primers and probes. The invention furthermore relates to oligonucleotides, compositions, solid phases and kits which may be used for carrying out the method of the invention.

22 Claims, 3 Drawing Sheets

Figure 1

|  |  | SEQ ID NO.: |
|---|---|---|
| Forward primer No. 1: | GTC GAT GGA CAA CGG GTT GAT (1854-F) | 1 |
| Forward primer No. 2: | GCG GTA CTA ACC ACC CAA AA (1915-F) | 3 |
| Forward primer No. 3: | GGACCTAAGGCGAGGCCG (54F) | 5 |
| Forward primer No. 4: | AGTGAGAATGCAGGCATGAG (1726) | 7 |
| Forward primer No. 5: | GCGTAATAGCTCACT (1023) | 9 |
|  |  |  |
| Reverse primer No. 1: | GGTACGGCTACCTTCCTGCGTCA (2052) | 2 |
| Reverse primer No. 2: | TTACCACTGACTGGTACGGCTA (2049) | 4 |
| Reverse primer No. 3: | GCCTTCCTGCGTCACCCC (2025) | 6 |
| Reverse primer No. 4: | CTTAGGATGGTTATAGTTACCA ( HCG II ) | 8 |
| Reverse primer No. 5: | CGGAACTTACCCGA | 10 |

Figure 2A

| Probe | SEQ ID | Related Target Organism | Sequence 5' to 3' |
|---|---|---|---|
| 1 | 11 | Mycobacterium avium | GCRTGGCGATTCGGG |
| 2 | 12 | Gram + with high GC content | CGACTACGCCTGTCGG |
| 3 | 13 | Mycobacterium celatum | GCACGGTCAGCGAGG |
| 4 | 14 | Mycobacterium chelonae | AGCGGGTTCACGTCG |
| 5 | 15 | Mycobacterium fortuitum 1 | GGATCAGTCACGACG |
| 6 | 16 | Mycobacterium fortuitum 2 | TGGTCACGGTGGTTT |
| 7 | 17 | Mycobacterium peregrinum | GGATCGGTCACGACG |
| 8 | 18 | Mycobacterium gordonae | TAGCACAATTGATTC |
| 9 | 19 | Mycobacterium malmoense | GTGGAGGTTCGGGGC |
| 10 | 20 | Mycobacterium phiei | ATCGGCCAGGTTTTG |
| 11 | 21 | Mycobacterium tuberculosis - complex | GGAGTTCTGGGGCTG |
| 12 | 22 | Mycobacterium xenopi | TTAGCAGATCCGATT |
| 13 | 23 | Mycobacterium intracellulare/ Mycobacterium scrophulaceum Mycobacterium interjectum | CCCCGAAACTCCAYGC |
| 14 | 24 | Mycobacterium intracellulare | ACGCSCATACACGGG |
| 15 | 25 | Mycobacterium scrophulaceum Mycobacterium interjectum | ACGCSCATATACGGG |
| 16 | 26 | Mycobacterium kansasii | GGGGCGTGGAGGTCT |
| 17 | 27 | Mycobacterium marinum | CAACGAACGTTCCAC |

Figure 2B

| Probe No. | SEQ ID NO.: | related target organism | Sequence 5' to 3' |
|---|---|---|---|
| 18 | 28 | Corynebacterium amycolatum | CCTGAACATGCGCCGT |
| 19 | 29 | Corynebacterium callunae | ACCACCCGAATGCCTCC |
| 20 | 30 | Corynebacterium diphteriae | CCATGGATCTGCTGG |
| 21 | 31 | Corynebacterium glutamicum | TCCATAAGCACCCGC |
| 22 | 32 | CDC Coryneform Group G | ACCACCGCGGATGCA |
| 23 | 33 | Corynebacterium jeikeium | ACCACCCTGAAGCGTG |
| 24 | 34 | Corynebacterium matrucchotii | ACTGCCTCGGGATCA |
| 25 | 35 | Corynebacterium minutissimun | CGATTGGGCGTGTTCT |
| 26 | 36 | Corynebacterium pseudodiphteriticum | CGTGTGAGACTCATTG |
| 27 | 37 | Corynebacterium pseudotuberculosis/ Corynebacterium ulcerans | TGTGTGGGTGTGTGT |
| 28 | 38 | Corynebacterium striatum | GTTACTGTGRTTASCCT |
| 29 | 39 | Corynebacterium xerosis | AGCATCCTTTCGTCAC |
| 30 | 40 | Nocardia asteroides | ATCCGGACGGATTCT |
| 31 | 41 | Rhodococcus equi | AGCCGCCTTCGAACCT |
| 32 | 42 | Tsukamurella paurometabolum | CACCTTGATCACCTTCG |

METHOD FOR DETECTING GRAM-POSITIVE BACTERIA

This application is a 371 of PCT/EP02/03956 filed Apr. 9, 2002, which claims priority to German Application No. 101 21 505.3 filed May 2, 2001.

FIELD OF THE INVENTION

The present invention relates to the field of diagnostics of microorganisms, in particular to detection of Gram-positive bacteria with high GC content, such as mycobacteria, in clinical diagnostics.

BACKGROUND OF THE INVENTION

The detection of bacteria and their accurate identification play a very important role in clinical diagnostics. Thus, a particular pathogen in bacterial infections should be identified as quickly as possible in order to be able to initiate an appropriate treatment.

In this context, Gram-positive bacteria, in particular mycobacteria, play an important part. Currently more than 100 mycobacterial species are known which have been detected and differentiated from clinical material. Pathogenic mycobacterial species such as the *Mycobacterium tuberculosis* complex, *Mycobacterium intracellulare* and *Mycobacterium avium* are of particular importance here.

In medical routine diagnostics and in food analysis, bacteria have traditionally been identified via selective media and subsequent investigation of the biochemical properties. Frequently, however, it is not possible here to determine the exact species. Moreover, these studies are very time-consuming, and a pure culture must be present for more extensive studies. Highly complex and diverse groups of bacteria with difficult growth conditions in particular are difficult to access by traditional culture differentiation and/or slow down diagnostics considerably due to their slow growth.

In recent years, nucleic acid-based methods have increasingly been introduced in order to detect bacteria. Said methods comprise, for example, carrying out nucleic acid amplification reactions using species-specific primers. Detection is usually via gel electrophoresis or via immobilized probes in microtiter plates. However, such techniques are not suitable for detecting one or more out of a multiplicity of possible pathogenic organisms. One approach to this problem is an amplification reaction mixture containing a mixture of different species-specific amplification primers and corresponding probes and/or a primer pair complementary to a base section of a group of organisms. The species specificity is ensured here via the structure of the probes.

The ribosomal RNA (rRNA) or ribosomal DNA (rDNA) including its spacer structures has already been used as target sequence for amplification of bacteria-specific nucleic acid. The target sequence most frequently used diagnostically is 16S rRNA. It is the best represented sequence in the appropriate databases. However, due to the relatively conserved character, species-characteristic sequence structures are not always found. In contrast, the 16S-23S rDNA spacer region is highly variable within many species and well suited to identifying bacteria. It is also superior to the 16S rRNA with respect to its structural information content. However, these target regions have also only limited suitability for distinguishing between a large number of mycobacterial species, since their sequence variability is too high and thus the sensitivity to probes against said target region decreases.

Liesack et al. (1991) FEBS Lett. 281, 114-118 disclose the complete nucleotide sequence of *Mycobacterium leprae* 23S and 5S rRNA and various target sequences for detection of bacteria. A probe of the *Helix* 54 region for detecting *Mycobacterium leprae* was disclosed, inter alia. This, however, does not allow the conclusion that it is possible to distinguish between a very large number of different species of Gram-positive bacteria with high GC content, for example mycobacteria, on the basis of the *Helix* 54 target region.

SUMMARY OF THE INVENTION

The present invention relates to a method for detecting and/or identifying Gram-positive bacteria with high GC content, according to which method first a nucleic acid amplification reaction is carried out and then a composition comprising the amplification product or a part thereof is hybridized with one or more probes. Finally, the degree of hybridization is determined.

Various reactions may be used as nucleic acid amplification reaction. Preference is given to using the polymerase chain reaction (PCR). The various designs of the PCR technique are known to the skilled worker, see, for example, Mullis (1990) Target amplification for DNA analysis by the polymerase chain reaction. Ann Biol Chem (Paris) 48(8), 579-582. Further amplification techniques which may be applied are nucleic acid strand-based amplification (NASBA), transcriptase mediated amplification (TMA), reverse transcriptase polymerase chain reaction (RT-PCR), Q-β replicase amplification (β-Q-Replicase) and single strand displacement amplification (SDA). NASBA and other transcription-based amplification methods are discussed in Chan and Fox, Reviews in Medical Microbiology (1999), 10(4), 185-196.

The nucleic acid amplification reaction is carried out using a sample composition. Said sample composition may be any composition which is suspected of containing bacteria, in particular Gram-positive bacteria with high GC content. It may be primary material, for example tracheal secretions, wound smears, blood etc., or cultures of microorganisms previously grown in liquid or on solid media.

According to the invention, the primer pair present in the nucleic acid amplification reaction is a first primer having any of the sequences SEQ ID NO. 1, SEQ ID NO. 3, SEQ ID NO. 5, SEQ ID NO. 7 or SEQ ID NO. 9 and a second primer having any of the sequences SEQ ID NO. 2, SEQ ID NO. 4, SEQ ID NO. 6, SEQ ID NO. 8 or SEQ ID NO. 10. The sequences of the individual primers are depicted in FIG. 1.

In a preferred embodiment, any of the primer pairs having the sequences

SEQ ID NO. 1/SEQ ID NO. 2 (primer pair 1),

SEQ ID NO. 3/SEQ ID NO. 4 (primer pair 2),

SEQ ID NO. 5/SEQ ID NO. 6 (primer pair 3),

SEQ ID NO. 7/SEQ ID NO. 8 (primer pair 4) and

SEQ ID NO. 9/SEQ ID NO. 10 (primer pair 5)

is present in the nucleic acid amplification reaction.

Any of said primer pairs may be used for amplifying a nucleic acid region which comprises at least part of the *Helix* 54 of 23S rDNA/rRNA of Gram-positive bacteria with high GC content. The primers may, in different combinations, amplify the *Helix* 54 region of all G+C-rich Gram-positive bacteria. The primer SEQ ID NO. 8 (FIG. 1), in particular, is capable of binding specifically only to nucleic acid of G+C-rich Gram-positive bacteria under suitable reaction conditions. The combination of primer SEQ ID NO. 3 (FIG. 1) with SEQ ID NO. 2 (FIG. 1) or with SEQ ID NO. 4 (FIG. 1) amplifies *M. chelonae* complex, *M. kansasii, M. malmoense, M. tuberculosis* complex, *M. avium, M. scrophulaceum* and *M. interjectum* in a highly specific manner.

The skilled worker appreciates that it is possible, starting from the teaching of the present invention, to design primers which deviate slightly from the primers of the invention but which function nevertheless. Thus, primers which are extended or truncated by at least one, two or three nucleotides at the 5' and/or 3' end compared to the inventive primers having the sequences SEQ ID NO. 1 to 10 are also conceivable. Extensions or truncations at the 5' end of the primers, in particular, may still provide functional primers which may be used according to the invention. Likewise, it is conceivable that individual or some nucleotides of a primer are replaced with other nucleotides, as long as the specificity of said primers and the melting temperature of said primers are not altered too much. It is evident to the skilled worker that, apart from the usual nucleotides A, G, C and T, modified nucleotides such as inosin etc. may also be applied. The teaching of the present invention makes such modifications possible, starting from the subject matter of the claims.

According to the invention, a composition comprising the amplification product or a part thereof is hybridized with one or more probes. The probes are oligonucleotides which have any of the sequences SEQ ID NO. 11 to 42 or the sequences complementary thereto. FIGS. 2A and 2B depict the sequences of the individual probes. Slight modifications of the probes are also conceivable, with negligible impairment of their functionality. The probes of the present invention may be extended and/or truncated by a few nucleotides, preferably by no more than three nucleotides, more preferably by no more than two nucleotides, most preferably by one nucleotide, at the 5' end and/or the 3' end. It is likewise possible to replace one or some nucleotides in the sequence of the probes of the invention with a different nucleotide, as long as hybridization to the target sequence is still possible. This includes the fact that in modifications the melting temperature of the modified probe does not deviate too much from the melting temperature of the original probe. The melting temperature is calculated according to the formula:

melting temperature=(number of *G/C* base pairs)·4° C.+

+(number of A/T base pairs)·2° C.

In principle, hybridization with a single specific probe can determine the bacterial species. However, it is also possible to hybridize the composition comprising the amplification product or a part thereof with more than one probe. This increases the meaningfulness of the method. The most accurate statement is possible if a hybridization is carried out with all probes having the sequences SEQ ID NO. 11 to 42 (or the sequences complementary thereto). In this case, an accurate profile is obtained and the bacterial species can be determined with great certainty. Thus, for example, probe SEQ ID NO. 23 (FIG. 2A) hybridizes with nucleic acid from the bacteria *M. intracellulare, M. scrophulaceum* and *M. interjectum*. *M. intracellulare*, however, may be removed from *M. scrophulaceum* and *M. interjectum* by probe SEQ ID NO. 24 (FIG. 2A). Probe SEQ ID NO. 25 (FIG. 2A) hybridizes with nucleic acid from *M. celatum, M. chelonae* complex, *M. gordonae, M. kansasii, M. malmoense, M. tuberculosis* complex, *M. scrophulaceum* and *M. interjectum* and other mycobacterial species but, as far as we know, only with species of the genus mycobacteria. It removes, together with SEQ ID NO. 23 (FIG. 2A), the species *M. scrophulaceum* and *M. interjectum* from all other mycobacteria, according to current knowledge. This is, in a similar way, also true for probe SEQ ID NO. 24.

The hybridization is usually carried out in such a way that either the composition comprising the amplification product or a part thereof or the probe is immobilized on a solid phase and contacted with the respective other hybridization partner. Possible solid phases are a large variety of materials, for example nylon, nitrocellulose, polystyrene, siliceous materials, etc. It is also possible to use a microtiter plate as solid phase.

Normally, at least one probe or at least one primer is labeled. A large variety of labels are possible such as, for example, fluorescent dyes, biotin or digoxigenin. Common fluorescent labels are fluorescein, FITC, cyanine dyes, etc. The labels are usually covalently linked to the oligonucleotides. Biotin and digoxigenin labels can be detected with suitable binding molecules after incubation, while a fluorescent label can be detected directly. A biotin-labeled oligonucleotide, for example, may be detected by contacting it with a solution containing streptavidin coupled to an enzyme, said enzyme, for example peroxidase or alkaline phosphatase, converting a substrate which generates a dye or produces chemiluminescence. Methods of this kind are known per se to the skilled worker.

In one embodiment of the invention, at least one of the primers used is labeled. Preferably, a plurality of the primers present in the reaction are labeled. If labeled primers are used, then the probes are usually not labeled. In this embodiment of the method, the probes are immobilized on a solid phase which is then contacted with the composition comprising the amplification product or a part thereof. This method is advantageous in that it is possible to immobilize more than one probe on the solid phase. Preference is given to immobilizing at least two probes, more preferably at least five probes, still more preferably at least ten probes, most preferably the probes having the sequences SEQ ID NO. 11 to 42 or the correspondingly complementary sequences, on the solid phase. Incubation of the amplification product or a part thereof with a solid phase with immobilized probes, which has been prepared in this way, can obtain, via a single hybridization step, information about hybridization of the amplification product with all immobilized probes. Therefore, the solid phase is preferably a microarray of immobilized probes on a solid phase. Such "DNA chips" allow immobilizing of a large number of different oligonucleotides on a small area. The solid phases suitable for DNA chips are preferably composed of siliceous materials such as glass etc. In this embodiment, the primer label is preferably a fluorescent label. The DNA chip may be rapidly analyzed by a scanning device, after incubation with the amplification product. Such devices are known to the skilled worker. A review of chip technology can be found in McGlennen (2001) Miniaturization technologies for molecular diagnostics, Clin Chem 47(3), 393-402.

In another embodiment, at least one of the probes has a label. In this case, the composition comprising the amplification product or a part thereof is usually immobilized on a solid phase and contacted with a composition comprising at least one probe selected from the group consisting of probes having the sequences SEQ ID NO. 11 to 42 and sequences complementary thereto. In this embodiment too, preference is given to carrying out a hybridization with more than one probe. For this purpose, it is possible to provide a plurality of solid phases on which the amplification product is immobilized. It is also possible, however, to immobilize small amounts of the amplification product on a plurality of spatially separated regions on a solid phase. These various spots are then contacted with in each case different probes (hybridization).

The procedure of the hybridization method is known per se to the skilled worker. Thus, after incubation with the solution which may contain the hybridization partner, the solid phases are usually subjected to stringent conditions in order to remove unspecifically bound nucleic acid molecules. The hybridization may be carried out in a conventional way on a nylon or nitrocellulose membrane, as described (Sambrook et al., Molecular Cloning, Cold Spring Harbor Laboratory, 1989). The principles mentioned therein can be transferred to further embodiments by the skilled worker.

According to the invention, the degree of hybridization is determined after hybridization. This is usually carried out by determining the amount of label bound to the solid phase. Detection reactions and detection methods of this kind are known per se to the skilled worker.

Another aspect of the invention is an oligonucleotide having any of the sequences SEQ ID NO. 1 to 42. The present invention likewise relates to an oligonucleotide having a sequence complementary to any of the sequences SEQ ID NO. 11 to 42.

The invention also relates to a composition comprising at least one such oligonucleotide. Preferably, the composition comprises a primer pair, with the first primer being selected from the group consisting of the primers having the sequences SEQ ID NO. 1, SEQ ID NO. 3, SEQ ID NO. 5, SEQ ID NO. 7 and SEQ ID NO. 9 and the second primer being selected from the group consisting of the primers having the sequences SEQ ID NO. 2, SEQ ID NO. 4, SEQ ID NO. 6, SEQ ID NO. 8 and SEQ ID NO. 10. More preferably, the composition comprises any of the primer pairs having the sequences SEQ ID NO. 1/SEQ ID NO. 2 (primer pair 1), SEQ ID NO. 3/SEQ ID NO. 4 (primer pair 2), SEQ ID NO. 5/SEQ ID NO. 6 (primer pair 3), SEQ ID NO. 7/SEQ ID NO. 8 (primer pair 4) and SEQ ID NO. 9/SEQ ID NO. 10 (primer pair 5).

Another aspect of the invention is a solid phase on which at least one oligonucleotide having any of the sequences SEQ ID NO. 11 to 42 or a sequence complementary thereto is immobilized. If a plurality of oligonucleotides are immobilized, said oligonucleotides are spatially separated from one another on the solid phase. In a preferred embodiment, the oligonucleotides having the sequences SEQ ID NO. 11 to 42 or a sequence complementary thereto are immobilized on the solid phase. The solid phase is preferably designed as DNA chip.

The invention furthermore relates to a kit for detecting and/or identifying Gram-positive bacteria with high GC content, in particular mycobacteria, which kit comprises at least one oligonucleotide of the invention. In a particular embodiment, said kit comprises at least one primer pair, the first primer being selected from the group consisting of the primers having the sequences SEQ ID NO. 1, SEQ ID NO. 3, SEQ ID NO. 5, SEQ ID NO. 7 and SEQ ID NO. 9 and the second primer being selected from the group consisting of the primers having the sequences SEQ ID NO. 2, SEQ ID NO. 4, SEQ ID NO. 6, SEQ ID NO. 8 and SEQ ID NO. 10; and at least one oligonucleotide having any of the sequences SEQ ID NO. 11 to 42 or the sequences complementary thereto. More preferably, the kit comprises any of the primer pairs having the sequences SEQ ID NO. 1/SEQ ID NO. 2 (primer pair 1), SEQ ID NO. 3/SEQ ID NO. 4 (primer pair 2), SEQ ID NO. 5/SEQ ID NO. 6 (primer pair 3), SEQ ID NO. 7/SEQ ID NO. 8 (primer pair 4) and SEQ ID NO. 9/SEQ ID NO. 10 (primer pair 5).

The preferred embodiments of the compositions, solid phases and kits of the present invention correspond to those of the method of the invention.

Finally, the invention also relates to the use of one or more of the oligonucleotides having the sequences SEQ ID NO. 1 to 10 as primers in a nucleic acid amplification reaction, in particular for detecting and/or identifying Gram-positive bacteria with high GC content.

The invention also relates to the use of one or more of the oligonucleotides having the sequences SEQ ID NO. 11 to 42 or sequences complementary thereto as probes in a hybridization reaction, in particular for detecting and/or identifying Gram-positive bacteria with high GC content.

The 23S rRNA/rDNA probes described herein and their application in the recognition and differentiation of bacteria of the phylogenetic branch of Gram-positive bacteria with high GC content are of great importance in medical microbiology. Normally said species can be differentiated by morphological or biochemical methods only with great difficulties and/or identification are slowed down considerably due to their slow growth. Conservative flanking regions make this gene region accessible to a nucleic acid amplification using a single set of primers (generic amplification primers). This makes it possible to use chip technology.

BRIEF DESCRIPTION OF THE DRAWINGS

FIG. 1 depicts the nucleic acid sequences of the primers having the sequences SEQ ID NO. 1 to 10.

FIG. 2A depicts a list of the probes having the sequences SEQ ID NO. 11 to 27 and the in each case related target organisms.

FIG. 2B depicts the sequences of the probes having the sequences SEQ ID NO. 28 to 42 and the in each case related target organisms.

DETAILED DESCRIPTION OF THE PREFERRED EMBODIMENTS

The following examples are intended to illustrate the invention in more detail.

Example 1

Isolation of DNA/RNA

Bacterial nucleic acid was obtained either from solid nutrient media, liquid media or from primary material, after appropriate preparation.

TABLE 1

Bacterial species studied in Example 1

| Species | Abbreviation | ATCC No. |
|---|---|---|
| Mycobacterium avium | M. avi | 25291 |
| Mycobacterium celatum | M. cel | |
| Mycobacterium chelonae | M. che | 14472 |
| Mycobacterium fortuitum | M. fo1 | 6841 |
| Mycobacterium fortuitum | M. fo2 | |
| Mycobacterium peregrinum | M. per | |
| Mycobacterium gordonae | M. gor | 14470 |

TABLE 1-continued

Bacterial species studied in Example 1

| Species | Abbreviation | ATCC No. |
|---|---|---|
| Mycobacterium malmoense | M. mal | 29571 |
| Mycobacterium phlei | M. phl | 11758 |
| Mycobacterium tuberculosis | M. tub | 27294 |
|  |  | 25177 |
| Mycobacterium xenopi | M. xen | 19971 |
| Mycobacterium intracellulare | M. int | 13950 |
| Mycobacterium scrophulaceum | M. scr | 19981 |
| Mycobacterium interjectum | M. itm |  |
| Mycobacterium kansasii | M. kan | 12478 |
| Mycobacterium marinum | M. mar | 827 |
| Escherichia coli | E. col |  |
| Human DNA | hDNA |  |
| Negative control | N-Kon |  |

For this purpose, bacterial material was removed from solid media using a sterile inoculation loop and suspended in 300 µl of 10 mM Tris/HCl pH 7.5. From liquid cultures, 1 ml was removed, centrifuged in a bench top centrifuge at 13,000 rpm for 5 min and, after discarding the supernatant, resuspended in 300 µl of 10 mM Tris/HCl pH 7.5. Primary material was liquefied with acetyl cysteine and "decontaminated" with NaOH/SDS. The cell suspensions obtained in this way were incubated in a Thermomixer (Eppendorf, Hamburg, Germany) at 95° C. for 15 min, sonicated in an ultrasound bath (Bandelin) for 15 min and centrifuged in a bench top centrifuge at 13,000 rpm for 10 min. In each case, 5 µl of the supernatant were used in the amplification reaction.

Amplification:

All primers were commercially synthesized (Interactiva, Ulm, Germany). The PCR mixture contained 1× Taq buffer (Qiagen, Hilden, Germany), 1 mM of each primer, 200 µM dNTP (Roche) and 1U of Hotstar Taq polymerase (Qiagen, Hilden, Germany). The PCR amplification was carried out on a Thermocycler PE 9600 (ABI, Weiterstadt, Germany), with 95° C. for 15 min, 10 cycles with 95° C. for 30 s and 60° C. for 2 min and with 20 cycles with 95° C. for 10 s, 55° C. for 50 s and 70° C. for 30 s.

The NucliSens amplification kit (Organon Technika, Boxtel, The Netherlands) was used according to the manufacturer's instructions for RNA amplification using the NASBA technique:
1. Preparation of the amplification mix: 8 µl "reagent sphere" in "reagent dilution" dissolved in buffer (contains the enzymes required for the reaction), 5 µl of KCl solution, final concentration 70 mM KCl and 2 µl of primer solution, final concentration 0.5 µM primer;
2. 5 µl of RNA solution added and incubated in a water bath at 41° C. for 60 min.

The DNA/RNA amplicon was detected either by using an agarose gel stained with ethidium bromide or by hybridization.

Detection of the Amplicons by Probe Hybridization:

All probes were biotinylated at the 5' end in order to be able to detect target sequence/probe hybrids via reporter enzymes coupled to streptavidin. The probes used are oligonucleotide sequences SEQ ID NO. 11 to 27 (see FIG. 2A).

Absorbent paper (Blotting Papier GB002, Schleicher & Schüll, Dassel, Germany) and a nylon membrane (Biodyne A, Pall, Portsmouth, England) were cut to the size of the blotting apparatus (Minifold Schleicher & Schüll, Dassel, Germany) and soaked with 10×SSC. 250 µl of denaturation solution (50 mM NaOH; 1.5 M NaCl) were first introduced into the openings of the assembled apparatus and 20 µl of amplicon were added using a pipette. After applying a vacuum, the liquid was allowed to be sucked through completely. This was followed by rinsing with 10×SSC buffer. After the membrane had dried completely, it was fixed in a UV crosslinker (UV-Stratalinker 2400, Stratagene, La Jolla, USA) at 1200 Joule/cm² and washed with distilled water and dried.

All hybridizations were carried out in glass tubes in a hybridization oven (Hybaid Mini Oven MkII, MWG-Biotech, Ebersberg, Germany) at 50° C. The membrane coated with DNA/RNA amplicon was rolled up in the dry state and placed into a glass tube. The membrane was then incubated with continuous rotation with prewarmed hybridization buffer for 5 min. After adding 2 pmol of biotinylated probe, the hybridization reaction took place for one hour. Unbound or only partially bound probe was removed by incubating with stringent buffer at 50° C. for 30 min with a single exchange of the prewarmed stringent buffer. This was followed by adding blocking reagent and further incubating at 37° C. for 15 min. The hybrids were detected via a streptavidin-alkaline phosphatase conjugate either calorimetrically by adding NBT/BCIP or autoradiographically by spraying on a chemiluminescent substrate (Lumi-Phos 530, Cellmark Diagnostics, Abindon, England). For this purpose, streptavidin-alkaline phosphatase conjugate was added, followed by incubation at 37° C. for 30 min. The membrane was subsequently washed twice with substrate buffer for 15 min each. The membrane was then removed, Lumi-Phos reagent was sprayed on, followed by exposure of an X-ray film for 2 h. Alternatively, substrate buffer containing NBT/BCIP was added and the color was allowed to develop.

Solutions Used

10×SSC solution (standard saline citrate):

1.5 M NaCl, 0.15M trisodium citrate;

Hybridization buffer:

7% SDS (sodium dodecyl sulfate), 0.25 M phosphate buffer pH 7.5;

Stringent washing solution (stringent buffer):

3 M TMCL (tetramethylammonium chloride), 50 mM Tris/Cl, 2 mM EDTA, 0.1% SDS;

Solution for saturating the membrane binding sites:

5 g/l blocking reagent (Roche) in maleic acid buffer pH 7.5 (4.13 g of NaCl and 5.53 g of maleic acid in 500 ml of water, pH adjusted to 7.5 with 5 M NaOH);

Substrate buffer:

274 mM Tris/Cl pH 7.5, 68.6 mM Na$_3$ citrate, 200 mM NaCl, 27.4 mM MgCl$_2$*6H$_2$O;

BCIP:

50 mg/ml 5-bromo-4-chloro-3-indonyl phosphate, toluidinium salt in 100% dimethylformamide;

NBT:

75 mg/ml nitroblue tetrazolium salt in 70% dimethylformamide;

The autoradiograms were evaluated densitometrically. The 100% base value used was the amplicondot of the species from which the probe sequence had been derived. Controls which were always carried along as dots on the membrane were a sample to which water rather than nucleic acid solution had been added and a sample containing 100 ng of isolated human DNA.

TABLE 2

Results of Example 1. The percentages of the densitometric evaluation are listed. The value of the probe homologous for the species was set to 100%. The probes used here may also have overlapping specificities.

| Probe Taxon | 1 | 2 | 3 | 4 | 5 | 6 | 7 | 8 | 9 |
|---|---|---|---|---|---|---|---|---|---|
| M. avi | 100.0 | 100.0 | 22.3 | 13.8 | 30.6 | 13.9 | 21.9 | 13.2 | 14.5 |
| M. cei | 11.1 | 100.0 | 100.0 | 19.8 | 22.5 | 08.6 | 11.3 | 18.1 | 10.2 |
| M. che | 14.0 | 75.4 | 21.1 | 100.0 | 11.2 | 14.8 | 10.4 | 20.7 | 12.9 |
| M. fo1 | 19.1 | 92.9 | 11.1 | 17.8 | 100.0 | 22.6 | 40.7 | 09.5 | 15.0 |
| M. fo2 | 11.3 | 100.0 | 12.6 | 18.8 | 27.6 | 100.0 | 34.0 | 10.0 | 11.4 |
| M. per | 17.3 | 100.0 | 24.8 | 19.4 | 14.2 | 11.4 | 100.0 | 22.8 | 14.6 |
| M. gor | 08.6 | 100.0 | 17.4 | 21.4 | 02.3 | 10.9 | 14.6 | 100.0 | 04.8 |
| M. mal | 08.4 | 94.7 | 12.8 | 19.7 | 09.6 | 11.4 | 14.2 | 17.5 | 100.0 |
| M. phl | 14.6 | 100.0 | 09.5 | 04.6 | 08.4 | 05.5 | 08.4 | 08.1 | 03.5 |
| M. tub | 17.8 | 88.6 | 11.6 | 18.1 | 20.1 | 14.2 | 12.8 | 18.4 | 14.8 |
| M. xen | 04.5 | 100.0 | 02.4 | 03.7 | 02.6 | 01.8 | 05.4 | 01.2 | 01.6 |
| M. int | 19.5 | 100.0 | 21.4 | 19.4 | 28.3 | 25.4 | 19.2 | 29.1 | 24.6 |
| M. scr | 20.1 | 87.3 | 19.4 | 24.5 | 27.4 | 20.3 | 20.8 | 20.1 | 22.9 |
| M. itm | 21.5 | 100.0 | 17.1 | 22.1 | 28.4 | 25.4 | 20.1 | 20.9 | 29.3 |
| M. kan | 09.1 | 79.3 | 08.5 | 09.4 | 08.1 | 09.9 | 10.2 | 08.8 | 07.4 |
| M. mar | 18.6 | 100.0 | 14.3 | 11.5 | 20.4 | 21.2 | 11.1 | 10.9 | 17.7 |
| E. col | 07.5 | 08.0 | 07.4 | 07.2 | 06.8 | 06.3 | 07.4 | 16.9 | 06.8 |
| hDNA | 0.1 | 0.2 | 0.02 | 0.04 | 0.05 | 0.1 | 0.06 | 0.1 | 0.05 |
| N-kon | 0.04 | 0.02 | 0.01 | 0.01 | 0.02 | 0.02 | 0.1 | 0.1 | 0.06 |

| Probe Taxon | 10 | 11 | 12 | 13 | 14 | 15 | 16 | 17 |
|---|---|---|---|---|---|---|---|---|
| M. avi | 24.1 | 10.4 | 09.1 | 31.1 | 80.3 | 34.1 | 16.2 | 14.6 |
| M. cei | 09.5 | 10.4 | 08.9 | 75.9 | 19.6 | 18.7 | 10.7 | 12.3 |
| M. che | 08.4 | 07.8 | 12.3 | 17.6 | 19.3 | 82.0 | 23.9 | 10.2 |
| M. fo1 | 08.9 | 09.4 | 11.3 | 19.2 | 11.9 | 19.6 | 10.8 | 06.4 |
| M. fo2 | 14.0 | 09.1 | 15.5 | 18.7 | 14.6 | 22.5 | 14.9 | 09.9 |
| M. per | 24.8 | 21.4 | 19.8 | 19.2 | 10.2 | 21.6 | 28.0 | 14.6 |
| M. gor | 14.5 | 17.5 | 14.1 | 20.1 | 01.8 | 88.2 | 09.9 | 10.4 |
| M. mal | 10.2 | 10.8 | 18.4 | 12.8 | 17.8 | 74.3 | 09.7 | 12.4 |
| M. phl | 100.0 | 01.9 | 09.6 | 11.8 | 09.8 | 04.1 | 05.3 | 02.4 |
| M. tub | 14.9 | 100.0 | 16.2 | 21.4 | 14.6 | 82.4 | 24.5 | 10.0 |
| M. xen | 01.6 | 01.7 | 100.0 | 01.4 | 02.0 | 02.1 | 01.4 | 01.8 |
| M. int | 20.0 | 34.7 | 18.9 | 100.0 | 100.0 | 41.4 | 15.0 | 19.7 |
| M. scr | 17.5 | 32.4 | 19.2 | 100.0 | 29.1 | 78.9 | 15.5 | 17.8 |
| M. itm | 19.4 | 38.4 | 24.6 | 100.0 | 34.0 | 100.0 | 11.8 | 10.8 |
| M. kan | 14.1 | 07.4 | 04.6 | 18.4 | 09.8 | 92.9 | 100.0 | 07.1 |
| M. mar | 19.5 | 22.8 | 12.3 | 10.8 | 08.4 | 10.5 | 14.8 | 100 |
| E. col | 07.9 | 07.8 | 08.4 | 07.2 | 07.4 | 07.4 | 07.8 | 06.1 |
| hDNA | 0.01 | 0.2 | 0.5 | 0.04 | 0.1 | 0.05 | 0.02 | 0.08 |
| N-kon | 0.04 | 0.09 | 0.2 | 0.06 | 0.06 | 0.01 | 0.01 | 0.04 |

The methods described here may be used to identify and differentiate the corresponding bacteria either from primary material (e.g. tracheal secretions, wound smears, blood, and the like) or from bacterial liquid or solid media. In the case of material which is not primarily sterile, the accompanying flora which is not acid-resistant must be removed beforehand by common decontamination methods. This applies both to the setting-up of the culture and to the preparation of the primary material.

Example 2

Using the methods according to Example 1, further samples containing Gram-positive bacteria with high GC content were studied. The bacterial species studied were:

TABLE 3

Bacterial species studied in Example 2

|  | ATCC No. |
|---|---|
| Corynebacterium amycolatum | C. amy |
| Corynebacterium callunae | C. cal |
| Corynebacterium diphteriae gravis | C. dpg |
| Corynebacterium glutamicum | C. glu |
| CDC Coryneform Group G | C. grG |
| Corynebacterium jeikeium | C. jei |
| Corynebacterium matrucchotii | C. mat |
| Corynebacterium minutissimun | C. min |
| Corynebacterium pseudodiphteriticum | C. pdp |
| Corynebacterium pseudotuberculosis | C. ptb |
| Corynebacterium ulcerans | C. ulc |
| Corynebacterium striatum | C. str |
| Corynebacterium xerosis | C. xer   373 |
| Nocardia asteroides | N. ast |
| Rhodococcus equi | R. equ |
| Tsukamurella paurometabolum | T. prm |

TABLE 3-continued

Bacterial species studied in Example 2

| | ATCC No. |
|---|---|
| *Escherichia coli* | E. col |
| Human DNA | hDNA |
| Negative Control | N-Kon |

The probes used are oligonucleotides having the sequences SEQ ID NO. 28 to 42 (see FIG. 2B).

The evaluation was likewise carried out as described in Example 1. The results are summarized in Table 4.

TABLE 4

Results of Example 2. The percentages of the densitometric evaluation are listed. The value of the probe homologous for the species was set to 100%. The probes used here may also have overlapping specificities.

| Probe Taxon | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|
| C. amy | 100.0 | 09.4 | 11.4 | 04.9 | 24.2 | 14.8 | 11.0 | 18.4 | 21.1 | 11.8 | 14.2 | 15.5 | 19.7 | 09.4 | 08.1 |
| C. cal | 19.5 | 100.0 | 11.7 | 18.8 | 20.8 | 20.0 | 11.8 | 14.6 | 14.5 | 18.4 | 19.2 | 12.1 | 11.5 | 18.6 | 18.4 |
| C. dpg | 14.4 | 18.5 | 100.0 | 12.7 | 17.6 | 13.7 | 14.4 | 19.4 | 20.0 | 26.1 | 09.7 | 11.1 | 17.8 | 13.2 | 17.1 |
| C. glu | 19.5 | 11.8 | 17.9 | 100.0 | 12.4 | 17.6 | 19.2 | 14.6 | 11.8 | 19.8 | 19.9 | 14.8 | 09.6 | 18.6 | 14.8 |
| C. grG | 21.9 | 12.8 | 18.2 | 18.3 | 100.0 | 15.8 | 20.3 | 11.6 | 14.4 | 15.9 | 22.1 | 13.5 | 17.6 | 11.2 | 15.9 |
| C. jei | 09.8 | 19.4 | 12.5 | 18.4 | 12.8 | 100.0 | 18.8 | 12.6 | 14.6 | 12.4 | 11.1 | 18.1 | 19.7 | 17.4 | 14.8 |
| C. mat | 15.4 | 13.6 | 13.8 | 12.7 | 17.6 | 16.5 | 100.0 | 10.9 | 11.7 | 11.2 | 13.5 | 15.8 | 17.2 | 12.5 | 19.7 |
| C. min | 18.5 | 14.6 | 13.8 | 17.6 | 12.6 | 12.1 | 20.5 | 100.0 | 15.4 | 16.4 | 17.6 | 17.4 | 12.5 | 04.6 | 22.9 |
| C. pdp | 15.2 | 16.6 | 17.1 | 11.2 | 20.1 | 08.6 | 15.4 | 14.9 | 100.0 | 08.9 | 18.4 | 18.4 | 13.8 | 14.8 | 20.1 |
| C. ptb | 14.6 | 14.6 | 18.6 | 17.6 | 14.2 | 14.3 | 18.5 | 14.8 | 18.7 | 100.0 | 23.4 | 11.3 | 10.9 | 17.3 | 28.1 |
| C. ulc | 16.4 | 16.9 | 21.4 | 18.6 | 15.4 | 13.5 | 17.2 | 17.5 | 17.4 | 100.0 | 24.9 | 12.3 | 10.0 | 19.1 | 27.4 |
| C. str | 05.6 | 19.4 | 14.6 | 12.4 | 18.4 | 16.9 | 13.3 | 12.1 | 14.1 | 18.2 | 100.0 | 10.2 | 10.9 | 19.5 | 20.4 |
| C. xer | 14.5 | 12.6 | 19.4 | 15.6 | 14.6 | 15.4 | 12.5 | 42.1 | 8 | 16.4 | 13.8 | 100.0 | 14.3 | 12.8 | 11.3 |
| N. ast | 07.4 | 08.1 | 09.2 | 10.3 | 04.2 | 03.6 | 08.8 | 04.6 | 09.5 | 10.8 | 02.6 | 11.5 | 100.0 | 08.5 | 05.2 |
| R. equ | 03.4 | 06.6 | 08.5 | 08.4 | 01.6 | 08.8 | 06.6 | 04.8 | 08.1 | 05.1 | 08.2 | 06.3 | 04.3 | 100.0 | 05.2 |
| T. prm | 04.3 | 02.6 | 06.5 | 02.9 | 09.4 | 06.6 | 06.3 | 08.2 | 08.6 | 01.6 | 05.4 | 08.4 | 04.2 | 03.6 | 100.0 |
| E. col | 08.5 | 05.3 | 07.1 | 05.5 | 04.2 | 04.2 | 09.1 | 07.2 | 01.4 | 05.4 | 04.1 | 02.2 | 08.5 | 05.1 | 04.2 |
| hDNA | 0.1 | 0.03 | 0.05 | 0.08 | 0.09 | 0.1 | 0.1 | 0.04 | 0.05 | 0.08 | 0.1 | 0.09 | 0.08 | 0.1 | 0.04 |
| N-kon | 0.02 | 0.02 | 0.01 | 0.03 | 0.01 | 0.02 | 0.1 | 0.504 | 0.08 | 0.02 | 0.01 | 0.1 | 0.08 | 0.08 | 0.02 |

What is claimed is:

1. A method for detecting and/or identifying Gram-positive bacteria with high GC content, which comprises:
   a) subjecting a sample composition to a nucleic acid amplification reaction, with there being a first primer sequence selected from the group consisting of SEQ ID NO. 1, SEQ ID NO. 3, SEQ ID NO. 5, SEQ ID NO. 7 and SEQ ID NO. 9 and there being a second primer sequence selected from the group consisting of SEQ ID NO. 2, SEQ ID NO. 4, SEQ ID NO. 6, SEQ ID NO. 8 and SEQ ID NO. 10;
   b) hybridizing a composition comprising the amplification product of step a) or a part thereof with one or more oligonucleotide probe sequences selected from any one of SEQ ID NO. 11 to 42 or sequences complementary thereto; and
   c) determining the degree of hybridization by reference to a control sample.

2. The method as claimed in claim 1, wherein the nucleic acid amplification reaction is a polymerase chain reaction.

3. The method as claimed in claim 1, wherein any of the primer pairs selected from the following sequence pairs:
   SEQ ID NO: 1/SEQ ID NO. 2 (primer pair 1),
   SEQ ID NO. 3/SEQ ID NO. 4 (primer pair 2),
   SEQ ID NO. 5/SEQ ID NO. 6 (primer pair 3),
   SEQ ID NO. 7/SEQ ID NO. 8 (primer pair 4) and
   SEQ ID NO. 9/SEQ ID NO. 10 (primer pair 5)
   is present in the nucleic acid amplification reaction.

4. The method as claimed in claim 1, wherein at least one primer is labeled with a label selected from the group consisting of fluorescent label, biotin, and digoxigenin, wherein said one or more oligonucleotide probe sequences are immobilized on a solid phase and wherein unbound components are washed off prior to detection.

5. The method as claimed in claim 1, wherein one or more probes are immobilized on a solid phase and said solid phase is then contacted with the composition comprising the amplification product of step a) or a part thereof.

6. The method as claimed in claim 1, wherein at least two probes are immobilized on a solid phase.

7. The method as claimed in claim 1, wherein the probes having the sequences selected from SEQ ID NO. 11 to 42 or a correspondingly complementary sequence are immobilized on a solid phase, the individual probes being immobilized in spatially separated regions of said solid phase.

8. The method as claimed in claim 1, wherein at least one of the probes has a label.

9. The method as claimed in claim 1, wherein the amplification product or a part thereof is immobilized on a solid phase and contacted with a composition comprising at least one probe sequence selected from the group consisting of SEQ ID NO. 11 to 42 and sequences complementary thereto.

10. An oligonucleotide sequence selected from the group consisting of the sequences SEQ ID NO. 1 to 42 and sequences complementary to the sequences SEQ ID NO. 11 to 42.

11. A composition comprising at least one oligonucleotide sequence, wherein said oligonucleotide sequence consists of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42, or a sequence complementary to a sequence consisting of SEO ID NO: 11, 12, 13, 14, 15, 16, 17, 18, 19, 20, 21, 22, 23, 24, 25, 26, 27, 28, 29, 30. 31, 32, 33, 34, 35, 36, 37, 38, 39, 40. 41, or 42.

12. The composition as claimed in claim 11, comprising at least one primer pair, wherein the first primer sequence consists of SEQ ID NO. 1, 3, 5, 7, or 9 and the second primer sequence consists of SEQ ID NO: 2, 4, 6, 8, or 10.

13. The composition as claimed in claim 12, comprising any one of the primer sequences pairs selected from:
   SEQ ID NO. 1/SEQ ID NO. 2 (primer pair 1),
   SEQ ID NO. 3/SEQ ID NO. 4 (primer pair 2),
   SEQ ID NO. 5/SEQ ID NO. 6 (primer pair 3),
   SEQ ID NO. 7/SEQ ID NO. 8 (primer pair 4), or
   SEQ ID NO. 9/SEQ ID NO. 10 (primer pair 5).

14. A solid phase on which at least one oligonucleotide sequence, wherein said oligonucleotide sequence consists of SEQ ID NO: 11, 12, 13, 14, 15, 16, 17, 18, 19, 20, 21, 22. 23, 24, 25, 26, 27, 28, 29, 30, 31, 32, 33, 34, 35, 36, 37, 38, 39, 40, 41, or 42, or a sequence complementary thereto are immobilized, the various oligonucleotides being spatially separated from one another.

15. A kit for detecting or identifying Gram-positive bacteria with high GC content, comprising at least one oligonucleotide sequence wherein said oligonucleotide sequence consists of SEQ ID NO: 11, 12, 13, 14, 15. 16, 17, 18, 19, 20, 21, 22, 23, 24, 25, 26, 27, 28, 29, 30, 31, 32, 33, 34, 35, 36, 37, 38, 39, 40, 41, or 42, or sequences complementary thereto.

16. The kit as claimed in claim 15, further comprising:
   a) at least one primer pair, wherein the first primer sequence consists of SEQ ID NO: 1, 3, 5, 7, or 9 and the second primer sequence consists of SEQ ID NO: 2, 4, 6, 8, or 10; and
   b) at least one oligonucleotide sequence wherein said oligonucleotide sequence consists of SEQ ID NO: 11. 12, 13, 14, 15, 16, 17, 18, 19. 20, 21, 22, 23, 24, 25. 26, 27, 28, 29, 30, 31, 32, 33, 34, 35, 36. 37, 38, 39, 40, 41, or 42, or sequences complementary thereto.

17. The kit as claimed in claim 15, further comprising any one of the primer pairs:
   SEQ ID NO: 1/SEQ ID NO. 2 (primer pair 1),
   SEQ ID NO. 3/SEQ ID NO. 4 (primer pair 2),
   SEQ ID NO. 5/SEQ ID NO. 6 (primer pair 3),
   SEQ ID NO. 7/SEQ ID NO. 8 (primer pair 4), or
   SEQ ID NO. 9/SEQ ID NO. 10 (primer pair 5).

18. A nucleic acid amplification method wherein an oligonucleotide which consists of any one of the sequence SEQ ID NO. 1 to 10 is used as a primer.

19. The nucleic acid amplification method of claim 18, wherein the oligonucleotide is used in the nucleic acid amplification reaction for detecting and/or identifying Gram-positive bacteria with high GC content.

20. A hybridization method wherein one or more of the oligonucleotide sequences selected from any one of SEQ ID NO. 11 to 42 or sequences complementary thereto is used as a probe.

21. The hybridization method of claim 20, wherein the oligonucleotide is used in the hybridization reaction for detecting and/or identifying Gram-positive bacteria with high GC content.

22. The method as claimed in claim 1, wherein at least one probe is labeled with a label selected from the group consisting of fluorescent label, biotin and digoxigenin wherein the composition comprising the amplification products is immobilized on a solid phase and wherein unbound components are washed off prior to detection.

* * * * *

SEQUENCE LISTING

<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gtcgatggac aacgggttga t                                              21

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
ggtacggcta ccttcctgcg tca                                            23

<210> SEQ ID NO 3
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 3
gcggtactaa ccacccaaaa                                                     20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
ttaccactga ctggtacggc ta                                                  22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
ggacctaagg cgaggccg                                                       18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
gccttcctgc gtcacccc                                                       18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
agtgagaatg caggcatgag                                                     20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
cttaggatgg ttatagttac ca                                                  22

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 9
gcgtaatagc tcact                                                          15

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 10
cggaacttac ccga                                                     14

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 11
gcrtggcgat tcggg                                                    15

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 12
cgactacgcc tgtcgg                                                   16

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 13
gcacggtcag cgagg                                                    15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 14
agcgggttca cgtcg                                                    15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 15
ggatcagtca cgacg                                                    15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Probe -continued

<400> SEQUENCE: 16
tggtcacggt ggttt                                                    15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 17
ggatcggtca cgacg                                                    15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 18
tagcacaatt gattc                                                    15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 19
gtggaggttc ggggc                                                    15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 20
atcggccagg ttttg                                                    15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 21
ggagttctgg ggctg                                                    15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 22
ttagcagatc cgatt                                                    15

<210> SEQ ID NO 23
<211> LENGTH: 16

-continued

```
<212> TYPE: DNA
<213> ORGANISM: Artificial Sequence
<220> FEATURE:
<223> OTHER INFORMATION: Description of Artificial Sequence: Probe

<400> SEQUENCE: 23
ccccgaaact ccaygc                                                   16

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 24
acgcscatac acggg                                                    15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 25
acgcscatat acggg                                                    15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 26
ggggcgtgga ggtct                                                    15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 27
caacgaacgt tccac                                                    15

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 28
cctgaacatg cgccgt                                                   16

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 29
```

```
accacccgaa tgcctcc                                                  17

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 30
ccatggatct gctgg                                                    15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 31
tccataagca cccgc                                                    15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 32
accaccgcgg atgca                                                    15

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 33
accaccctga agcgtg                                                   16

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 34
actgcctcgg gatca                                                    15

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 35
cgattgggcg tgttct                                                   16

<210> SEQ ID NO 36
<211> LENGTH: 16
<212> TYPE: DNA
<213> ORGANISM: Artificial Sequence
```

```
<220> FEATURE:
<223> OTHER INFORMATION: Description of Artificial Sequence: Probe

<400> SEQUENCE: 36
cgtgtgagac tcattg                                                    16

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 37
tgtgtgggtg tgtgt                                                     15

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 38
gttactgtgr ttascct                                                   17

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 39
agcatccttt cgtcac                                                    16

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Probe

<400> SEQUENCE: 40
atccggacgg attct                                                     15

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 41
agccgccttc gaacct                                                    16

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 42
caccttgatc accttcg                                                   17
```